(12) United States Patent
Brown

(10) Patent No.: US 7,223,390 B2
(45) Date of Patent: May 29, 2007

(54) INSERTION OF FURIN PROTEASE CLEAVAGE SITES IN MEMBRANE PROTEINS AND USES THEREOF

(75) Inventor: Dennis T. Brown, Raleigh, NC (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 10/841,787

(22) Filed: May 7, 2004

(65) Prior Publication Data

US 2004/0224391 A1 Nov. 11, 2004

Related U.S. Application Data

(60) Provisional application No. 60/469,126, filed on May 9, 2003.

(51) Int. Cl.
*A01N 63/00* (2006.01)
(52) U.S. Cl. .................... 424/93.2; 435/6; 435/463; 435/219; 424/93.6
(58) Field of Classification Search ............. 424/185.1, 424/204.1, 218.1; 536/23.1
See application file for complete search history.

(56) References Cited

U.S. PATENT DOCUMENTS

| | | | |
|---|---|---|---|
| 5,357,041 A | 10/1994 | Roberts et al. | |
| 5,491,130 A | 2/1996 | Roberts et al. | |
| 5,770,563 A | 6/1998 | Roberts et al. | |
| 5,849,701 A | 12/1998 | Roberts et al. | |
| 6,051,549 A | 4/2000 | Roberts et al. | |
| 6,140,059 A * | 10/2000 | Schawaller | 435/7.1 |
| 6,384,189 B1 | 5/2002 | Murphy-Ullrich | |
| 6,458,767 B1 | 10/2002 | Murphy-Ullrich | |
| 6,562,598 B1 | 5/2003 | Himmelspach et al. | |
| 6,566,073 B1 | 5/2003 | Rivera et al. | |

FOREIGN PATENT DOCUMENTS

WO    WO 98/38318    9/1998

OTHER PUBLICATIONS

GenBank Accession # P08491, P08768.*
Chang et al. Nucleotide sequence of the genome region encoding the 26S mRNA of eastern equine encephaloyelitis virus and the deduced amino acid sequence of the viral structural proteins. Journal of General Virology (1987) vol. 68, No. 8, pp. 2129-2142.*
Kieffer et al., "Proteolytic processing of human zona pellucida proteins," *Biol. Reproduction*, 66:407-414, 2002.
McKnight et al., "Deduced consensus sequence of sindbis virus strain AR339: mutations contained in laboratory strains which affect cell culture and in vivo phenotypes," *J. Virol.*, 70:1981-1989, 1996.
Moehring et al., "Expression of mouse furin in a Chinese hamster cell resistant to pseudomonas exotoxin a and viruses complements the genetic lesion," *J. Biol. Chem.*, 268:2590-2594, 1993.
Phinney et al. "Sindbis virus glycoprotein E1 is divided into two discrete domains at amino acid 129 by disulfide bridge connections," *J. Virol.*, 74:9313-9316, 2000.
Zhang et al., "Mutations that promote furin-independent growth of semliki forest virus affect p62-E1 interactions and membrane fusion," *Virology*, 327:287-296, 2004.
Zimmer et al., "Proteolytic activation of respiratory syncytial virus fusion protein," *J. Biol. Chem.*, 276:31642-31650, 2001.
Bolt et al., "Cleavage of the respiratory syncytial virus fusion protein is required for its surface expression: role of furin," *Virus Res.*, 68:25-33, 2000.

(Continued)

*Primary Examiner*—Brenda Brumback
*Assistant Examiner*—Sharon Hurt
(74) *Attorney, Agent, or Firm*—Fulbright & Jaworski LLP

(57) ABSTRACT

Cleavage site for the protease furin is inserted between domains of a membrane glycoprotein. Upon cleavage by furin in the trans-Golgi network, the protein is separated into individual membrane-free domain that retains its native conformation. This protocol can be used to produce virus membrane protein domains for structural analysis and for trials as vaccines.

13 Claims, 3 Drawing Sheets

OTHER PUBLICATIONS

Smit et al., "PE2 cleavage mutants of sindbis virus: correlation between viral infectivity and pH-dependent membrane fusion activation of the spike heterodimer," *J. Virol.*, 75:11196-112904, 2001.
Supplementary European search report. Apr. 27, 2006.
Roberts, et al.: *Peptides and Their Utility in modulation of behavior of cells expressing α3 β1 Integrins*, WO 2001/005812, Jan. 25, 2001.
Hugo, et al.: *Thrombospondin Peptides are Potent Inhibitors of Mesangial and Glomerular Endothelial Cell Proliferation* in Vitro and in Vivo; *International Society of Nephrology*; 1999, vol. 55, pp. 2236-2249.

Shafiee, et al.: *Inhibition of Retinal Angiogenesis by Peptide Derived From Thrombospondin-1; IOVS*, Jul. 2000, vol. 41, No. 8., pp. 2378-2388.
Bogdanov, et al. *Treatment of Experimental Brain Tumors with Thrombospondin-1 Derived Peptides: an* in Vivo *Imaging Study; Neoplasia*; Nov. 1999, vol. 1, No. 5, pp. 438-445.
Neng-Hua Guo, et al. *Antiproliferative and Antitumor Activities of D-reverse Peptides Derived From the Second Type-1 Repeat of Thrombospondin-1; Journal of Peptide Research*; May. 1997, vol. 50, pp. 210-221.

* cited by examiner

INSERTION OF FURIN PROTEASE CLEAVAGE SITES IN MEMBRANE PROTEINS AND USES THEREOF

CROSS-REFERENCE TO RELATED APPLICATION

This non-provisional patent application claims benefit of provisional patent application U.S. Ser. No. 60/469,126, filed May 9, 2003, now abandoned.

The United States government may own certain rights to this invention pursuant to grant number AI 42775 from the National Institutes of Health.

BACKGROUND OF THE INVENTION

1. Field of the Invention

The present invention relates generally to the study and uses of membrane glycoproteins. More specifically, the present invention provides a method of producing membrane-free membrane glycoproteins maintained in native conformation.

2. Description of the Related Art

Many membrane glycoproteins are assembled within cells in a highly constrained and energy rich conformation. The membrane proteins of membrane-containing viruses are examples of energy rich proteins. These proteins assemble in the endoplasmic reticulum (ER) through intermediates which are stabilized by disulfide bonds. Because of this high energy configuration it is difficult if not impossible to maintain these proteins in native conformation when extracting them from their associated membrane. Extracting these proteins from the membrane results in their collapse into a normative, relaxed configuration that makes structural analysis on these proteins difficult. In the case of virus membrane proteins, the normative conformation makes these proteins ineffective for use as subunit viral vaccines.

In the case of influenza virus, this conformation problem was overcome by the discovery of an accessible protease site in the HA1-HA2 membrane glycoprotein (Wiley and Skehel, 1977). This site allowed the release of the protein ectodomain upon treatment of intact virus with the protease. The released ectodomain retained its native conformation, thereby allowing the determination of its structure at atomic resolution by X-ray crystallography (Wiley and Skehel, 1977).

Most membrane proteins, however, do not contain an accessible protease site such as that found in influenza virus. This fact and the failure of other methods of protein purification have made it impossible to obtain these proteins in native conformation. Thus, the prior art is deficient in a method of producing membrane-free membrane glycoproteins maintained in native conformation. The present invention provides a solution to this long-standing need and desire in the art.

SUMMARY OF THE INVENTION

The present invention provides a procedure of using naturally occurring cellular proteases to produce membrane protein domains that maintain native conformation upon release from their membrane bilayers. This event of proteolytic cleavage and release occurs after the protein has been exported from the endoplasmic reticulum and thus after the process of disulfide bridge formation, folding and oligomerization with other proteins (if necessary) occurs. After engaging the furin protease in the Golgi apparatus, the protein is converted to a nonmembrane-associated species which can be purified from the growth media by protocols that prevent loss of native conformation. This protocol provides new opportunities for the production of virus membrane protein domains for structural analysis and for trials as vaccines.

Virus carrying the furin insertion can be grown to high titer in host cells that do not express furin. These mutant viruses may be used as vaccines because when injected into mammalian host, these viruses would infect and begin the process of assembly but "self destruct" at the last stage of protein assembly at the trans Golgi network.

Thus, in one embodiment, the present invention comprises a method of producing a membrane glycoprotein domain, wherein the domain is membrane-free and is maintained in native conformation. This method may comprise the steps of: inserting a furin cleavage sequence in a region that divides the glycoprotein into separate domains; expressing the glycoprotein in a host cell; cutting the glycoprotein by furin in the trans-Golgi network of the host cell, thereby producing a membrane glycoprotein domain; secreting the glycoprotein domain from the host cell; and purifying the glycoprotein domain from the culture medium of the host cell, wherein the domain is membrane-free and is maintained in native conformation.

In another embodiment, the present invention comprises a method of producing a domain of alphavirus membrane glycoprotein useful as a subunit vaccine candidate, wherein said domain is membrane-free and is maintained in native conformation. This method generally comprises the steps of: inserting a furin cleavage sequence in a region that divides the glycoprotein into separate domains; expressing the glycoprotein in a host cell; cutting the glycoprotein by furin in the trans-Golgi network of the host cell, thereby producing a membrane glycoprotein domain; secreting the glycoprotein domain from the host cell; and purifying the glycoprotein domain from the culture medium of the host cell, wherein the domain is membrane-free and is maintained in native conformation.

In another embodiment, the present invention comprises a method of producing vaccine candidates for alphavirus. This method comprises the steps of inserting a furin cleavage sequence in a region that divides a membrane glycoprotein of the alphavirus into separate domains; incorporating sequence encoding the membrane glycoprotein comprising the furin cleavage sequence into a vector encoding the alphavirus; expressing the alphavirus in a host cell that does not express furin; and collecting alphaviruses produced by the host cell, wherein the collected viruses are vaccine candidates for alphavirus.

Other and further aspects, features, and advantages of the present invention will be apparent from the following description of the presently preferred embodiments of the invention. These embodiments are given for the purpose of disclosure.

DETAILED DESCRIPTION OF THE INVENTION

Furin is a protease which resides in the trans-Golgi network of eukaryotic cells (Moehring et al., 1993). Its function is to cleave proteins at a step just prior to their delivery to their final cellular destination. Furin recognizes a consensus amino acid sequence, RXRR (SEQ ID NO. 1), RXRK (SEQ ID NO. 2) or KXKR (SEQ ID NO. 3) (where X is any amino acid, Moehring et al., 1993) and cuts proteins which contain these sequences when they reach the trans-Golgi network.

In the present invention, a furin cleavage site is introduced into an exposed (externally situated) domain of a membrane glycoprotein. The modified protein will go through its normal process of folding and assembly to attain its native configuration. These events are required for its export from the endoplasmic reticulum. After export from the endoplasmic reticulum, the protein travels along the secretory pathway to reach the cell surface. When the protein reaches the trans-Golgi network, it is cleaved by the furin protease. The proteolytic event releases the ectodomain of the protein from the membrane bilayer without compromising its conformation. The protein is now a secreted protein and can be purified from the surrounding media by an appropriate purification protocol.

To demonstrate the feasibility of this process, the membrane glycoprotein E1 of the prototype alphavirus Sindbis virus was chosen as a model. The alphaviruses are representatives of a class of viruses (arboviruses) which are responsible for significant human disease such as Dengue Fever, West Nile Fever, Venezuelan Encephalitis, Yellow Fever etc. There are over 600 of these agents known but only one effective vaccine (against Yellow Fever) is currently available. Attempts to produce vaccines by producing subunits of extracted virus proteins or denatured virus have failed because of the loss of native protein conformation as described above.

The E1 glycoprotein of Sindbis virus is assembled in the endoplasmic reticulum of virus-infected cells into a compact, highly constrained and energy rich configuration. Correct folding is a prerequisite for its export from the endoplasmic reticulum to the cell surface. Attempts to remove the virus E1 protein from the membrane result in the loss of native conformation as disulfide bridges shuffle bringing the protein to a normative configuration.

Figure 1:
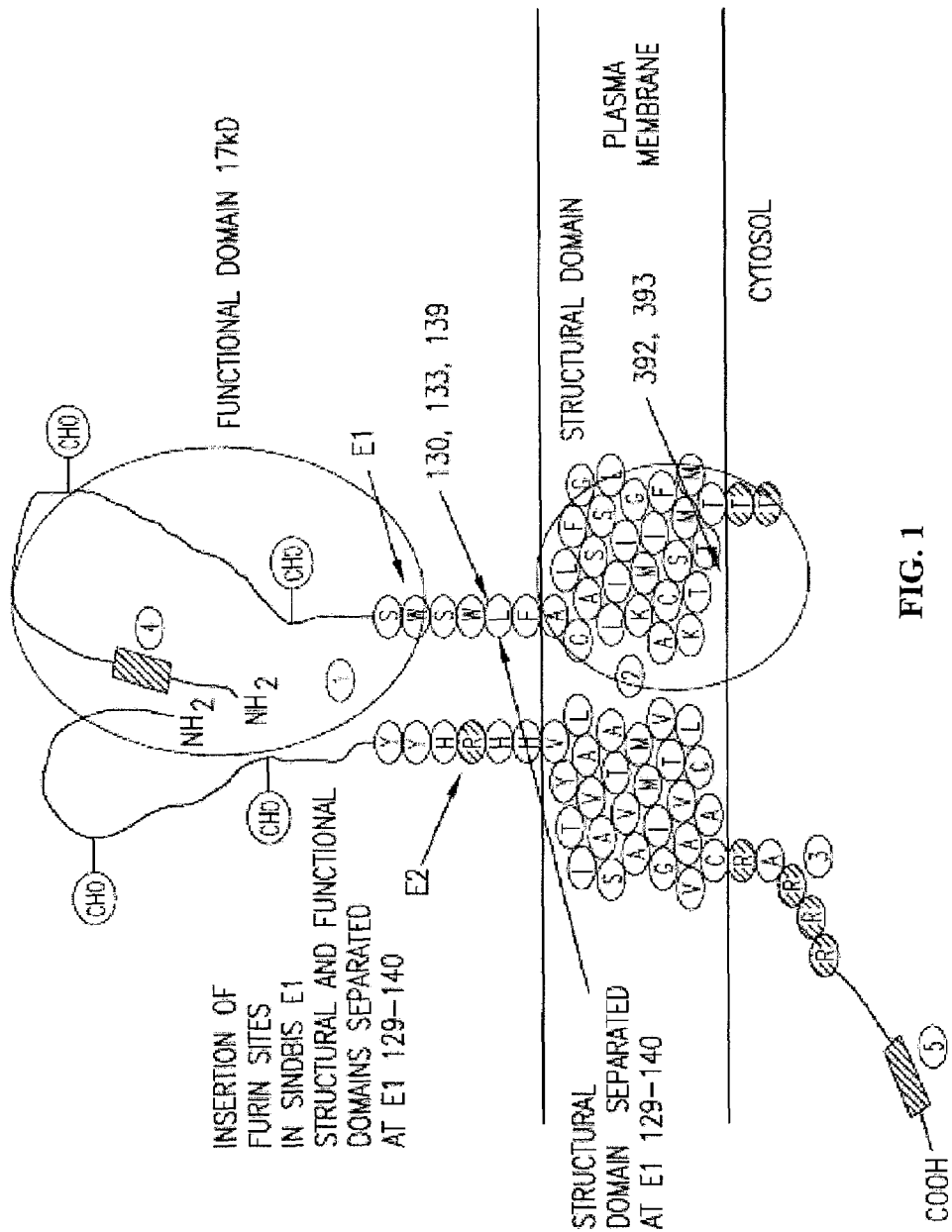
FIG. 1: Functional and structural domains in the E1 glycoprotein of Sindbis virus are separated by amino acids 129-140. Inserting furin cleavage sites at residue 130, 133 or 139 would cleave the protein into the 17 kD functional domain (which is released from the membrane) and the structural domain (which is retained in the membrane). Sites at E1 392 and 393 would release the entire ecto domain.

It has been shown that a correctly folded form of this protein is divided into two separate disulfide bridge stabilized domains and that the junction between these two domains is around amino acid E1-129 (Mulvey and Brown, 1994) (FIG. 1). The first of these domains (amino acids 1-129) contains the function of membrane penetration (functional domain), while the second domain (130-398) holds the icosahedral lattice intact (structural domain). Data presented below indicate that insertion of a furin cleavage site in the region separating the functional domain and the structural domain results in releasing the functional domain in native conformation from the membrane protein complex.

The choice of the sites where the furin cleavage site should be inserted can be determined based on the structure of the protein or, in case where the structure is not available, biochemical and/or sequence analyses. In general, the sites should be within segments of predominantly polar and or charged residues, most likely to be on the surface of the protein. If the three dimensional structure is known, the insertion sites should be in surface loops connecting well-ordered secondary structure elements with extensive hydrophobic interface.

When the structure of the protein is not available, hydrophobicity-based methods, secondary structure prediction methods and sequence alignment of homologues can often help reveal such candidate sites. If a small amount of the protein is available, limited proteolytic digestion followed by chromatographic co-fractionation and N-terminal polypeptide sequencing/mass spectroscopy can help determine such candidate sites which are accessible to protease digestion and nonessential for forming an integral protein structure. Cutting at such site would separate the protein into individual domains.

The instant method of obtaining membrane-free membrane glycoprotein can be applied to a number of viruses such as HIV, Herpes viruses, coronaviruses etc. In general, the furin cleavage site can be inserted into any virus membrane protein if that virus can replicate in a CHO cell line deficient in the protease furin or in a furin defective cell line that supports replication of the virus. The released membrane-free ecto domain of the viral glycoprotein can be used as a subunit vaccine.

In another embodiment, high titer of virus particles carrying the furin insertion can be generated in furin negative mammalian host cells. These viruses can be potential vaccine candidates. When injected into mammalian host, these viruses would infect and begin the process of assembly but 'self destruct" at the last stage of protein assembly at the trans Golgi network due to cleavage by furin. This approach would work for many viruses (e.g. HIV, Herpes etc) whenever furin-minus cell lines are available to support the growth of the mutant viruses.

As used herein, "membrane glycoprotein" refers to any integral membrane protein which is assembled in the endoplasmic reticulum and delivered to final destination by a cellular route that passes through the trans Golgi network.

As used herein, "membrane-free membrane glycoprotein" refers to an integral membrane protein which has been released from its membrane by cutting the protein at some point in the ectodomain with a protease.

As used herein, "native conformation" refers to the conformation achieved by a protein as it is folded in the endoplasmic reticulum. For viral protein, it also refers to the functional form exists in a mature infectious virus.

The present invention is directed to a method of producing a membrane glycoprotein domain, wherein said domain is membrane-free and is maintained in its native conformation. In one embodiment, this method can be used to produce a domain of a viral membrane glycoprotein such as an alphavirus membrane glycoprotein. The resulting viral membrane glycoprotein domain is useful as a subunit vaccine candidate.

First of all, a furin cleavage sequence is inserted in a region that divides the membrane glycoprotein into separate domains. In general, suitable regions include the surface of the protein, a surface loop or a region with predominant polar residues. Preferably, the furin cleavage sequence is SEQ ID NOs. 1, 2 or 3. Upon expression of such modified glycoprotein in a host cell, the glycoprotein would be separated into different domains by furin cleavage in the trans-Golgi network. Subsequently, the glycoprotein domains can be purified from the culture medium of the host cell, wherein the purified domains are membrane-free and are maintained in native conformation.

The present invention is also directed to a method of producing vaccine candidates for alphavirus. The method involves inserting a furin cleavage sequence in a region that would divide a membrane glycoprotein of alphavirus into separate domains. In general, suitable regions include the surface of the protein, a surface loop or a region with predominant polar residues. Preferably, the furin cleavage sequence is SEQ ID NOs. 1, 2 or 3 or a fragment or obvious variant of one of these furin cleavage sequences. The modified glycoprotein is then incorporated into a vector encoding the alphavirus and expressed in host cells that do not express furin. Alphaviruses produced by these host cells would be vaccine candidates for alphavirus.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Release of Protein Domain in Native Conformation After Furin Cleavage

To release the first domain of the E1 glycoprotein of Sindbis virus from the membrane protein complex, a furin protease cleavage site was inserted in the region separating the functional domain from the structural domain of the protein. This was done using the Quick-Change™ technique of mutagenesis (Stratagene) in a full length cDNA clone of the virus RNA (Rice et al., 1987).

The primers used to produce these mutations are shown in Table 1. Mutations were made to place the furin sensitive sequence at positions E1-130 (RXRK, SEQ ID NO.2), E1-133 (KXKR, SEQ ID NO.3) and E1-139 (RXRR, SEQ ID NO.1) using the naturally occurring amino acid sequences when possible. Selection of these sites was based on research which demonstrates that these sites would be exposed on the protein surface and thus would be available for protease cleavage (Phinney et al., 2000; Phinney and Brown, 2000).

It is predicted that these mutations would result in the release of the distal E1 protein domain from the E1 protein upon exposure to the cell associated enzyme furin. This would change the molecular weight of the intact E1 protein from a molecular weight of 58 kD to two proteins of molecular weights approximately 17 kD and 41 kD. To control for the effects of amino acid changes on the normal folding of the virus glycoproteins, the mutation-containing virus RNAs were transfected into a CHO (Chinese Hamster Ovary) cell line which does not have the furin protease (CHO-RPE40) (Moehring et al., 1993; Moehring and Moehring, 1983).

Figure 2:
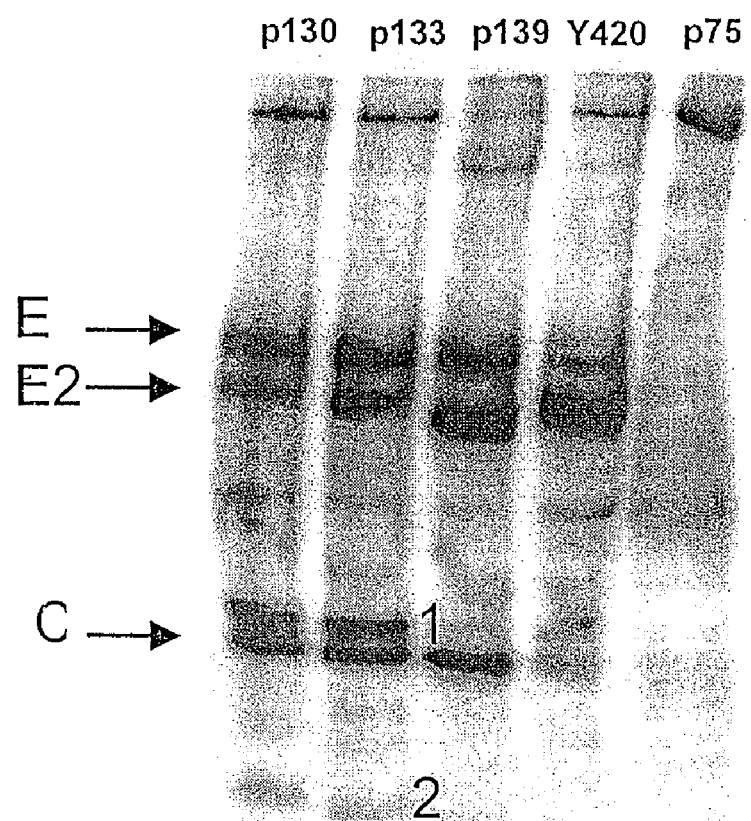
FIG. 2: Polyacrylamide gel electrophoresis of proteins produced by Sindbis virus mutants containing furin cleavage sites in the E1 glycoprotein. Numerical designation indicates the amino acid site in E1 where cleavage should occur. Y420, wild-type virus; P75, non-virus messenger RNA; E1, envelope protein 1; E2, envelope protein 2; C, capsid protein.

FIG. 2 shows proteins produced in mammalian cells transfected with constructs for the E1 mutants F130, F133 and F139. Placement of the cleavage site at positions E1-130 and E1-133 resulted in the production of new protein species migrating at molecular weights of approximately 41 and 17 kD as predicted. The amount of the 17 kD protein was relatively small as the proteins shown were those which were associated with the cell and it is likely that most of the 17 kD protein was secreted into the media. These proteins were not seen in the wild type transfection (Y420) or in cells transfected with a non-virus message (P75).

E1 393 mutant was intended to release the entire E1 ectodomain (see FIG. 1). The SDS PAGE of proteins immunoprecipitated from the media of BHK cells transfected with the RNA of the 393 mutant are shown in FIG. 3.

As was the case with mutant E1 139, mutation at E1 392 failed to produce the desired phenotype (data not shown). The transfection of BHK cells with RNA produced from the cDNA clone of mutant furin E1 392 resulted in the release into the media a protein migrating faster than glycoprotein E2 and which was immunoprecipitated by antibody against the whole virus. Wild-type E1 has 439 amino acids (58 kDa), wild-type E2 has 423 amino acids (53 kDa), and the truncated E1 ectodomain is predicted to have 392 amino acids (51 kDa), having lost 47 amino acids from the carboxyl terminus.

Figure 3:
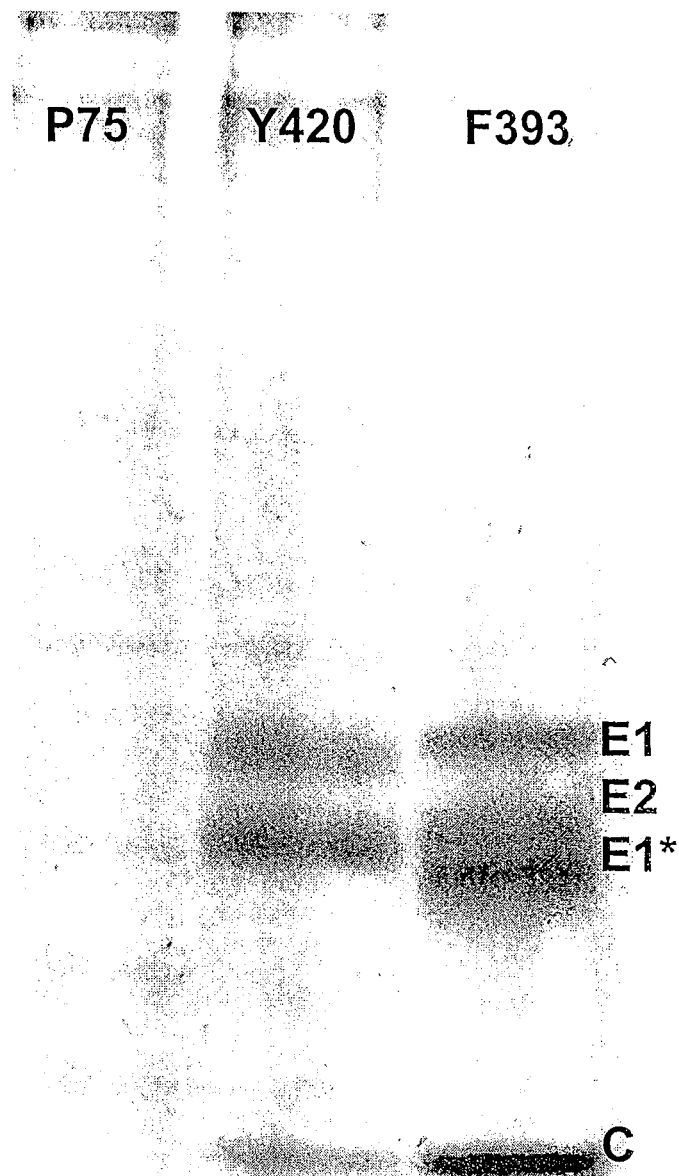
FIG. 3: Polyacrylamide gel electrophoresis of proteins produced by Sindbis virus mutants containing furin cleavage sites at position E1 393 (F393). The proteins are designated E1, E2 for the two normal virus glycoproteins and E1* for the furin truncated E1 protein. C is capsid protein. P75, a mutant containing a non-virus RNA, Y420, wild-type virus.

As shown in FIG. 3, E1 393 mutant (F393) produced more truncated E1 than wild-type E1, indicating that there was efficient processing at the 393 cleavage site.

TABLE 1

Primer Sets For The Production of
E1 Furin Sensitive Mutations

| Mutant | | Primer set | SEQ ID NO. |
|---|---|---|---|
| F-130 | Sense | 5'GCACACTCGCGCGCGGAAAGTAGG 3' | 4 |
| | Antisense | 5'CCTACTTTCCGCGCGCGAGTGTGC 3' | 5 |
| F-133 | Sense | 5'CCGCGATGAAAGTAAAACGCCGTATTGTGTACG 3' | 6 |
| | Antisense | 5'CCGTACTCAATACGGCGTTTTACTTTCATGCGG 3' | 7 |
| F-139 | Sense | 5'CTACGGGAGGACTAGGAGATTCCTAGATGTGT 3' | 8 |
| | Antisense | 5'ACACATCTAGGAATCTCCTAGTCCTCCCGTAC 3' | 9 |

TABLE 1-continued

Primer Sets For The Production of
E1 Furin Sensitive Mutations

| Mutant | | Primer set | SEQ ID NO. |
|---|---|---|---|
| F-392 | Sense | 5' GAGCACCCCGAGACACAAAAGAGACCAAGAATTTC 3' | 10 |
| | Antisense | 5' GAAATTCTTGGTCTCTTTTGTGTCTCGGGGTGCTC 3' | 11 |
| F-393 | Sense | 5' GAGCACCCCGCACAGAAATAGACGAGAATTTCAAGC 3' | 12 |
| | Antisense | 5' GCCGGCTTGAAATTCTCGTCTATTTCTGTGCGGGGT 3' | 13 |

EXAMPLE 2

Replication of Viruses Carrying the Furin Insertion

The effects of furin protease site insertions on the production of infectious virus are shown in Table 2. Table 2 shows that mutants containing the furin cleavage site produce very low levels of infectious virus when their RNA is transfected into the furin protease containing BHK-21 cells.

In contrast, these mutants produce wild-type (Y420) amounts of virus when transfected into CHO-RPE40 cells that do not have furin activity. For the mutants F-130 and F-133, this result shows that the presence of the furin cleavage site at these locations does not prevent correct folding E1 as it is incorporated into infectious virus. Infectious viruses production is inhibited by 5-6 orders of magnitude in the BHK cell because furin has cut the folded E1 protein into two separate domains. The mutant F-139 shows a similar inhibition of growth in BHK cells even though significant cleavage of E1 does not take place. In the case of the 139 substitution, the location of this mutation eliminates one of two glycosylation sites (Pletnev et al., 2001) as evidenced by the faster migration of this partially glycosylated protein. That elimination of glycosylation site may lead to conformational change that prevents infectious virus production.

The E1 393 mutant produced a titer of $10^3$ virions from BHK cells compared to a titer of $10^9$ produced by wild-type virus under similar conditions of RNA transfection. Mutant 393 produced $10^7$ to $10^8$ virions/ml in CHO RPE-40 cells (furin negative cells). Thus, the E1 393 mutant had significantly less virus production than wild-type or E1 130 and E1 133 mutants (Table 2). The reason for this difference is not clear but may imply a reduced efficiency of folding or oligomer formation in the furin 393-substituted glycoprotein.

TABLE 2

Replication of E1 Furin Mutants

| Mutant | Growth in BHK-21 | Growth in CHO-RPE40 |
|---|---|---|
| Y420 (wild type) | $1.0 \times 10^9$ | $1.25 \times 10^{10}$ |
| F 130 | $4.0 \times 10^4$ | $5.23 \times 10^{10}$ |
| F 133 | $4.4 \times 10^5$ | $5.13 \times 10^{10}$ |
| F 139 | $5.8 \times 10^4$ | $1.95 \times 10^{10}$ |
| F 393 | $10^3$ | $10^7$–$10^8$ |

The following references were cited herein:

Moehring et al., Expression of mouse furin in a Chinese hamster cell resistant to *Pseudomonas exotoxin* A and viruses complements the genetic lesion. *J Biol. Chem.* 268:2590-4 (1993).

Moehring and Moehring, Strains of CHO-K1 cells resistant to *Pseudomonas exotoxin* A and cross-resistant to diphtheria toxin and viruses. *Infect. Immun.* 41:998-1009 (1983).

Mulvey and Brown, Formation and rearrangement of disulfide bonds during maturation of the Sindbis virus E1 glycoprotein. *J. Virol.* 68:805-812 (1994).

Phinney and Brown, Sindbis virus glycoprotein E1 is divided into two discrete domains at amino acid 129 by disulfide bridge connections. *J Virol.* 74:9313-6 (2000).

Phinney et al., The surface conformation of Sindbis virus glycoproteins E1 and E2 at neutral and low pH, as determined by mass spectrometry-based mapping. *J Virol.* 74:5667-78 (2000).

Pletnev et al., Locations of carbohydrate sites on alphavirus glycoproteins show that E1 forms an icosahedral scaffold. *Cell* 105:127-36 (2001).

Rice et al., Production of infectious RNA transcripts from Sindbis virus cDNA clones: mapping of lethal mutations, rescue of a temperature-sensitive marker, and in vitro mutagenesis to generate defined mutants. *J Virol.* 61:3809-19 (1987).

Wiley and Skehel, Crystallization and x-ray diffraction studies on the haemagglutinin glycoprotein from the membrane of influenza virus. *J Mol. Biol.* 112:343-7 (1977).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A non-native, recombinant virus comprising an inserted furin cleavage sequence in a membrane glycoprotein such that furin cleavage releases an ectodomain of said glycoprotein from the membrane and wherein the membrane glycoprotein is an arbovirus membrane glycoprotein.

2. The virus of claim 1, wherein the inserted furin cleavage sequence is RXRR (SEQ ID NO. 1).

3. The virus of claim 1, wherein the inserted furin cleavage sequence is RXRK (SEQ ID NO. 2).

4. The virus of claim 1, wherein the inserted furin cleavage sequence is KXKR (SEQ ID NO. 3).

5. The virus of claim 1, wherein the inserted furin cleavage sequence is introduced into an exposed domain of said membrane glycoprotein.

6. The virus of claim 5, wherein the inserted furin cleavage site is in a surface loop.

7. The virus of claim 1, wherein said virus self destructs upon injection into a mammalian host.

8. The virus of claim 1, wherein 100 times more infectious virus is produced from host cells that lack furin expression as compared to host cells that express furin.

9. The virus of claim 8, wherein 1,000 times more infectious virus is produced from host cells that lack furin expression as compared to host cells that express furin.

10. The virus of claim 1, wherein the membrane glycoprotein is a Dengue, West Nile, Venezuelan Encephalitis, or Yellow Fever virus membrane glycoprotein.

11. The virus of claim 1, wherein the membrane glycoprotein is a Sindbis virus membrane glycoprotein.

12. The virus of claim 11, wherein the Sindbis virus membrane glycoprotein is the Sindbis virus E1 membrane glycoprotein.

13. The virus of claim 12, wherein the Sindbis virus E1 membrane glycoprotein comprises an inserted furin cleavage site at amino acid position 130, 133 or 393.

* * * * *

SEQUENCE LISTING

<160> NUMBER OF SEQ ID NOS: 13

<210> SEQ ID NO 1
<211> LENGTH: 4
<212> TYPE: PRT
<213> ORGANISM: Unknown
<220> FEATURE:
<221> NAME/KEY: DOMAIN
<222> LOCATION: 2
<223> OTHER INFORMATION: consensus amino acid sequence for furin
      cleavage site; Xaa is any amino acid

<400> SEQUENCE: 1

Arg Xaa Arg Arg

<210> SEQ ID NO 2
<211> LENGTH: 4
<212> TYPE: PRT
<213> ORGANISM: Unknown
<220> FEATURE:
<221> NAME/KEY: DOMAIN
<222> LOCATION: 2
<223> OTHER INFORMATION: consensus amino acid sequence for furin
      cleavage site; Xaa is any amino acid

<400> SEQUENCE: 2

Arg Xaa Arg Lys

<210> SEQ ID NO 3
<211> LENGTH: 4
<212> TYPE: PRT
<213> ORGANISM: Unknown
<220> FEATURE:
<221> NAME/KEY: DOMAIN
<222> LOCATION: 2
<223> OTHER INFORMATION: consensus amino acid sequence for furin
      cleavage site; Xaa is any amino acid

<400> SEQUENCE: 3

Lys Xaa Lys Arg

<210> SEQ ID NO 4
<211> LENGTH: 24
<212> TYPE: DNA
<213> ORGANISM: Artificial Sequence
<220> FEATURE:
<221> NAME/KEY: primer_bind
<223> OTHER INFORMATION: sense primer for mutant F130

<400> SEQUENCE: 4
gcacactcgc gcgcggaaag tagg                                              24

<210> SEQ ID NO 5
<211> LENGTH: 24
<212> TYPE: DNA
<213> ORGANISM: Artificial Sequence
<220> FEATURE:
<221> NAME/KEY: primer_bind
<223> OTHER INFORMATION: anti-sense primer for mutant F130

<400> SEQUENCE: 5
cctactttcc gcgcgcgagt gtgc                                              24

<210> SEQ ID NO 6
<211> LENGTH: 33
<212> TYPE: DNA

<213> ORGANISM: Artificial Sequence
<220> FEATURE:
<221> NAME/KEY: primer_bind
<223> OTHER INFORMATION: sense primer for mutant F133

<400> SEQUENCE: 6
ccgcgatgaa agtaaaacgc cgtattgtgt acg					33

<210> SEQ ID NO 7
<211> LENGTH: 33
<212> TYPE: DNA
<213> ORGANISM: Artificial Sequence
<220> FEATURE:
<221> NAME/KEY: primer_bind
<223> OTHER INFORMATION: anti-sense primer for mutant F133

<400> SEQUENCE: 7
ccgtactcaa tacggcgttt tactttcatg cgg					33

<210> SEQ ID NO 8
<211> LENGTH: 32
<212> TYPE: DNA
<213> ORGANISM: Artificial Sequence
<220> FEATURE:
<221> NAME/KEY: primer_bind
<223> OTHER INFORMATION: sense primer for mutant F139

<400> SEQUENCE: 8
ctacgggagg actaggagat tcctagatgt gt					32

<210> SEQ ID NO 9
<211> LENGTH: 32
<212> TYPE: DNA
<213> ORGANISM: Artificial Sequence
<220> FEATURE:
<221> NAME/KEY: primer_bind
<223> OTHER INFORMATION: anti-sense primer for mutant F139

<400> SEQUENCE: 9
acacatctag gaatctccta gtcctcccgt ac					32

<210> SEQ ID NO 10
<211> LENGTH: 35
<212> TYPE: DNA
<213> ORGANISM: Artificial Sequence
<220> FEATURE:
<221> NAME/KEY: primer_bind
<223> OTHER INFORMATION: sense primer for mutant F392

<400> SEQUENCE: 10
gagcaccccg agacacaaaa gagaccaaga atttc					35

<210> SEQ ID NO 11
<211> LENGTH: 35
<212> TYPE: DNA
<213> ORGANISM: Artificial Sequence
<220> FEATURE:
<221> NAME/KEY: primer_bind
<223> OTHER INFORMATION: anti-sense primer for mutant F392

<400> SEQUENCE: 11
gaaattcttg gtctcttttg tgtctcgggg tgctc					35

<210> SEQ ID NO 12
<211> LENGTH: 36
<212> TYPE: DNA
<213> ORGANISM: Artificial Sequence -continued

```
<220> FEATURE:
<221> NAME/KEY: primer_bind
<223> OTHER INFORMATION: sense primer for mutant F393

<400> SEQUENCE: 12
gagcaccccg cacagaaata gacgagaatt tcaagc                              36

<210> SEQ ID NO 13
<211> LENGTH: 36
<212> TYPE: DNA
<213> ORGANISM: Artificial Sequence
<220> FEATURE:
<221> NAME/KEY: primer_bind
<223> OTHER INFORMATION: anti-sense primer for mutant F393

<400> SEQUENCE: 13
gccggcttga aattctcgtc tatttctgtg cggggt                              36
```